(12) United States Patent
Bouwstra et al.

(10) Patent No.: US 7,192,926 B2
(45) Date of Patent: Mar. 20, 2007

(54) USE OF RECOMBINANT GELATIN-LIKE PROTEINS AS PLASMA EXPANDERS AND COMPOSITIONS SUITABLE FOR PLASMA SUBSTITUTION

(75) Inventors: Jan Bastiaan Bouwstra, Bilthoven (NL); Yuzo Toda, Goirle (NL)

(73) Assignee: Fuji Photo Film B.V., Tilburg (NL)

(*) Notice: Subject to any disclaimer, the term of this patent is extended or adjusted under 35 U.S.C. 154(b) by 0 days.

(21) Appl. No.: 10/658,989

(22) Filed: Sep. 10, 2003

(65) Prior Publication Data
US 2005/0101531 A1 May 12, 2005

(30) Foreign Application Priority Data
Sep. 11, 2002 (EP) .................... 02078745

(51) Int. Cl.
*A61K 38/16* (2006.01)
*C07H 21/04* (2006.01)

(52) U.S. Cl. ........................ 514/12; 536/23.1

(58) Field of Classification Search ............... 514/12; 424/678, 679, 680, 681
See application file for complete search history.

(56) References Cited

U.S. PATENT DOCUMENTS

| | | | |
|---|---|---|---|
| 2,827,419 A | | 3/1958 | Tourtellotte et al. |
| 3,057,782 A | | 10/1962 | Lindner et al. |
| 4,539,204 A | * | 9/1985 | Ecanow et al. ............ 514/6 |
| 6,150,081 A | | 11/2000 | Van Heerde et al. |
| 6,413,742 B1 | * | 7/2002 | Olsen et al. ............ 435/69.1 |

2005/0119170 A1 6/2005 Bouwstra et al.

FOREIGN PATENT DOCUMENTS

| | | |
|---|---|---|
| EP | 1238675 | 9/2002 |
| WO | WO 01/34646 A2 * | 5/2001 |
| WO | WO 0134646 | 5/2001 |

OTHER PUBLICATIONS

Haemaccel package insert (published Aug. 28, 1992).*
Nahas, G. et al. Prog Clin Biol Res. 19: 259-264 (1978).*
James N. Purtell, et al.; "Isoelectric point of albumin: Effect on renal handling of albumin"; Kidney International; vol. 16 (1979), pp. 366-376.
Partial European Search Report, EPA 02078745.3, Feb. 27, 2003.

* cited by examiner

*Primary Examiner*—Jon Weber
*Assistant Examiner*—Anand Desai
(74) *Attorney, Agent, or Firm*—Kirkpatrick & Lockhart Nicholson Graham LLP

(57) ABSTRACT

The invention relates to compositions suitable for plasma substitution comprising as a plasma expander a recombinant gelatin-like protein. Characteristic is that the gelatin-like protein can be a monomer or a polymer like a dimer, trimer or a tetramer of a human recombinant gelatin-like protein having an isolectric point of less than 8. The resulting gelatin-like proteins provide a method to control the clearance rate of a plasma expander by its molecular weight. Preferably the gelatin-like proteins have a low hydroxyproline content which prevents the composition from gelling and thus allows the use of high-molecular weight proteins in order to establish a suitable colloid osmotic pressure. An additional advantage of the gelatin-like proteins is that these avoid the risk of anaphylactic shock that exists in conjunction with the use of commercially available preparations.

30 Claims, 2 Drawing Sheets

SEQUENCE LISTING

<160> NUMBER OF SEQ ID NOS: 4

<210> SEQ ID NO 1
<211> LENGTH: 209
<212> TYPE: PRT

<213> ORGANISM: Artificial sequence
<220> FEATURE:
<223> OTHER INFORMATION: Hu-1

<400> SEQUENCE: 1

```
Gly Pro Pro Gly Glu Pro Gly Pro Thr Gly Leu Pro Gly Pro Pro Gly
1               5                   10                  15

Glu Arg Gly Gly Pro Gly Ser Arg Gly Phe Pro Gly Ala Asp Gly Val
            20                  25                  30

Ala Gly Pro Lys Gly Pro Ala Gly Glu Arg Gly Ser Pro Gly Pro Ala
        35                  40                  45

Gly Pro Lys Gly Ser Pro Gly Glu Ala Gly Arg Pro Gly Glu Ala Gly
    50                  55                  60

Leu Pro Gly Ala Lys Gly Leu Thr Gly Ser Pro Gly Ser Pro Gly Pro
65                  70                  75                  80

Asp Gly Lys Thr Gly Pro Pro Gly Pro Ala Gly Gln Asp Gly Arg Pro
                85                  90                  95

Gly Pro Pro Gly Pro Pro Gly Ala Arg Gly Gln Ala Gly Val Met Gly
            100                 105                 110

Phe Pro Gly Pro Lys Gly Ala Ala Gly Glu Pro Gly Lys Ala Gly Glu
        115                 120                 125

Arg Gly Val Pro Gly Pro Pro Gly Ala Val Gly Pro Ala Gly Lys Asp
    130                 135                 140

Gly Glu Ala Gly Ala Gln Gly Pro Pro Gly Pro Ala Gly Pro Ala Gly
145                 150                 155                 160

Glu Arg Gly Glu Gln Gly Pro Ala Gly Ser Pro Gly Phe Gln Gly Leu
                165                 170                 175

Pro Gly Pro Ala Gly Pro Pro Gly Glu Ala Gly Lys Pro Gly Glu Gln
            180                 185                 190

Gly Val Pro Gly Asp Leu Gly Ala Pro Gly Pro Ser Gly Pro Ala Gly
        195                 200                 205

Gly
```

<210> SEQ ID NO 2
<211> LENGTH: 617
<212> TYPE: PRT
<213> ORGANISM: Artificial sequence
<220> FEATURE:
<223> OTHER INFORMATION: Hu-3

<400> SEQUENCE: 2

```
Gly Pro Pro Gly Glu Pro Gly Pro Thr Gly Leu Pro Gly Pro Pro Gly
1               5                   10                  15

Glu Arg Gly Gly Pro Gly Ser Arg Gly Phe Pro Gly Ala Asp Gly Val
            20                  25                  30

Ala Gly Pro Lys Gly Pro Ala Gly Glu Arg Gly Ser Pro Gly Pro Ala
        35                  40                  45

Gly Pro Lys Gly Ser Pro Gly Glu Ala Gly Arg Pro Gly Glu Ala Gly
    50                  55                  60

Leu Pro Gly Ala Lys Gly Leu Thr Gly Ser Pro Gly Ser Pro Gly Pro
65                  70                  75                  80

Asp Gly Lys Thr Gly Pro Pro Gly Pro Ala Gly Gln Asp Gly Arg Pro
                85                  90                  95

Gly Pro Pro Gly Pro Pro Gly Ala Arg Gly Gln Ala Gly Val Met Gly
            100                 105                 110

Phe Pro Gly Pro Lys Gly Ala Ala Gly Glu Pro Gly Lys Ala Gly Glu
```

-continued

```
            115                 120                 125
Arg Gly Val Pro Gly Pro Pro Gly Ala Val Gly Pro Ala Gly Lys Asp
        130                 135                 140
Gly Glu Ala Gly Ala Gln Gly Pro Pro Gly Pro Ala Gly Pro Ala Gly
145                 150                 155                 160
Glu Arg Gly Glu Gln Gly Pro Ala Gly Ser Pro Gly Phe Gln Gly Leu
                165                 170                 175
Pro Gly Pro Ala Gly Pro Pro Gly Glu Ala Gly Lys Pro Gly Glu Gln
            180                 185                 190
Gly Val Pro Gly Asp Leu Gly Ala Pro Gly Pro Ser Gly Pro Ala Gly
        195                 200                 205
Glu Pro Gly Pro Thr Gly Leu Pro Gly Pro Pro Gly Glu Arg Gly Gly
    210                 215                 220
Pro Gly Ser Arg Gly Phe Pro Gly Ala Asp Gly Val Ala Gly Pro Lys
225                 230                 235                 240
Gly Pro Ala Gly Glu Arg Gly Ser Pro Gly Pro Ala Gly Pro Lys Gly
                245                 250                 255
Ser Pro Gly Glu Ala Gly Arg Pro Gly Glu Ala Gly Leu Pro Gly Ala
            260                 265                 270
Lys Gly Leu Thr Gly Ser Pro Gly Ser Pro Gly Pro Asp Gly Lys Thr
        275                 280                 285
Gly Pro Pro Gly Pro Ala Gly Gln Asp Gly Arg Pro Gly Pro Pro Gly
    290                 295                 300
Pro Pro Gly Ala Arg Gly Gln Ala Gly Val Met Gly Phe Pro Gly Pro
305                 310                 315                 320
Lys Gly Ala Ala Gly Glu Pro Gly Lys Ala Gly Glu Arg Gly Val Pro
                325                 330                 335
Gly Pro Pro Gly Ala Val Gly Pro Ala Gly Lys Asp Gly Glu Ala Gly
            340                 345                 350
Ala Gln Gly Pro Pro Gly Pro Ala Gly Pro Ala Gly Glu Arg Gly Glu
        355                 360                 365
Gln Gly Pro Ala Gly Ser Pro Gly Phe Gln Gly Leu Pro Gly Pro Ala
    370                 375                 380
Gly Pro Pro Gly Glu Ala Gly Lys Pro Gly Glu Gln Gly Val Pro Gly
385                 390                 395                 400
Asp Leu Gly Ala Pro Gly Pro Ser Gly Pro Ala Gly Glu Pro Gly Pro
                405                 410                 415
Thr Gly Leu Pro Gly Pro Pro Gly Glu Arg Gly Gly Pro Gly Ser Arg
            420                 425                 430
Gly Phe Pro Gly Ala Asp Gly Val Ala Gly Pro Lys Gly Pro Ala Gly
        435                 440                 445
Glu Arg Gly Ser Pro Gly Pro Ala Gly Pro Lys Gly Ser Pro Gly Glu
    450                 455                 460
Ala Gly Arg Pro Gly Glu Ala Gly Leu Pro Gly Ala Lys Gly Leu Thr
465                 470                 475                 480
Gly Ser Pro Gly Ser Pro Gly Pro Asp Gly Lys Thr Gly Pro Pro Gly
                485                 490                 495
Pro Ala Gly Gln Asp Gly Arg Pro Gly Pro Pro Gly Pro Pro Gly Ala
            500                 505                 510
Arg Gly Gln Ala Gly Val Met Gly Phe Pro Gly Pro Lys Gly Ala Ala
        515                 520                 525
Gly Glu Pro Gly Lys Ala Gly Glu Arg Gly Val Pro Gly Pro Pro Gly
    530                 535                 540
```

```
Ala Val Gly Pro Ala Gly Lys Asp Gly Glu Ala Gly Gln Gly Pro
545                 550                 555                 560

Pro Gly Pro Ala Gly Pro Ala Gly Glu Arg Gly Glu Gln Gly Pro Ala
            565                 570                 575

Gly Ser Pro Gly Phe Gln Gly Leu Pro Gly Pro Ala Gly Pro Pro Gly
            580                 585                 590

Glu Ala Gly Lys Pro Gly Glu Gln Gly Val Pro Gly Asp Leu Gly Ala
            595                 600                 605

Pro Gly Pro Ser Gly Pro Ala Gly Gly
            610                 615
```

<210> SEQ ID NO 3
<211> LENGTH: 821
<212> TYPE: PRT
<213> ORGANISM: Artificial sequence
<220> FEATURE:
<223> OTHER INFORMATION: Hu-4

<400> SEQUENCE: 3

```
Gly Pro Pro Gly Glu Pro Gly Pro Thr Gly Leu Pro Gly Pro Pro Gly
1               5                   10                  15

Glu Arg Gly Gly Pro Gly Ser Arg Gly Phe Pro Gly Ala Asp Gly Val
            20                  25                  30

Ala Gly Pro Lys Gly Pro Ala Gly Glu Arg Gly Ser Pro Gly Pro Ala
            35                  40                  45

Gly Pro Lys Gly Ser Pro Gly Glu Ala Gly Arg Pro Gly Glu Ala Gly
            50                  55                  60

Leu Pro Gly Ala Lys Gly Leu Thr Gly Ser Pro Gly Ser Pro Gly Pro
65                  70                  75                  80

Asp Gly Lys Thr Gly Pro Pro Gly Pro Ala Gly Gln Asp Gly Arg Pro
            85                  90                  95

Gly Pro Pro Gly Pro Pro Gly Ala Arg Gly Gln Ala Gly Val Met Gly
            100                 105                 110

Phe Pro Gly Pro Lys Gly Ala Ala Gly Glu Pro Gly Lys Ala Gly Glu
            115                 120                 125

Arg Gly Val Pro Gly Pro Pro Gly Ala Val Gly Pro Ala Gly Lys Asp
            130                 135                 140

Gly Glu Ala Gly Ala Gln Gly Pro Pro Gly Pro Ala Gly Pro Ala Gly
145                 150                 155                 160

Glu Arg Gly Glu Gln Gly Pro Ala Gly Ser Pro Gly Phe Gln Gly Leu
            165                 170                 175

Pro Gly Pro Ala Gly Pro Pro Gly Glu Ala Gly Lys Pro Gly Glu Gln
            180                 185                 190

Gly Val Pro Gly Asp Leu Gly Ala Pro Gly Pro Ser Gly Pro Ala Gly
            195                 200                 205

Glu Pro Gly Pro Thr Gly Leu Pro Gly Pro Pro Gly Glu Arg Gly Gly
            210                 215                 220

Pro Gly Ser Arg Gly Phe Pro Gly Ala Asp Gly Val Ala Gly Pro Lys
225                 230                 235                 240

Gly Pro Ala Gly Glu Arg Gly Ser Pro Gly Pro Ala Gly Pro Lys Gly
            245                 250                 255

Ser Pro Gly Glu Ala Gly Arg Pro Gly Glu Ala Gly Leu Pro Gly Ala
            260                 265                 270

Lys Gly Leu Thr Gly Ser Pro Gly Ser Pro Gly Pro Asp Gly Lys Thr
            275                 280                 285
```

-continued

Gly Pro Pro Gly Pro Ala Gly Gln Asp Gly Arg Pro Gly Pro Pro Gly
            290                 295                 300

Pro Pro Gly Ala Arg Gly Gln Ala Gly Val Met Gly Phe Pro Gly Pro
305                 310                 315                 320

Lys Gly Ala Ala Gly Glu Pro Gly Lys Ala Gly Glu Arg Gly Val Pro
                325                 330                 335

Gly Pro Pro Gly Ala Val Gly Pro Ala Gly Lys Asp Gly Glu Ala Gly
            340                 345                 350

Ala Gln Gly Pro Pro Gly Pro Ala Gly Pro Ala Gly Glu Arg Gly Glu
        355                 360                 365

Gln Gly Pro Ala Gly Ser Pro Gly Phe Gln Gly Leu Pro Gly Pro Ala
    370                 375                 380

Gly Pro Pro Gly Glu Ala Gly Lys Pro Gly Glu Gln Gly Val Pro Gly
385                 390                 395                 400

Asp Leu Gly Ala Pro Gly Pro Ser Gly Ala Gly Glu Pro Gly Pro
                405                 410                 415

Thr Gly Leu Pro Gly Pro Pro Gly Glu Arg Gly Gly Pro Gly Ser Arg
        420                 425                 430

Gly Phe Pro Gly Ala Asp Gly Val Ala Gly Pro Lys Gly Pro Ala Gly
    435                 440                 445

Glu Arg Gly Ser Pro Gly Pro Ala Gly Pro Lys Gly Ser Pro Gly Glu
    450                 455                 460

Ala Gly Arg Pro Gly Glu Ala Gly Leu Pro Gly Ala Lys Gly Leu Thr
465                 470                 475                 480

Gly Ser Pro Gly Ser Pro Gly Pro Asp Gly Lys Thr Gly Pro Pro Gly
            485                 490                 495

Pro Ala Gly Gln Asp Gly Arg Pro Gly Pro Pro Gly Pro Pro Gly Ala
        500                 505                 510

Arg Gly Gln Ala Gly Val Met Gly Phe Pro Gly Pro Lys Gly Ala Ala
    515                 520                 525

Gly Glu Pro Gly Lys Ala Gly Glu Arg Gly Val Pro Gly Pro Pro Gly
    530                 535                 540

Ala Val Gly Pro Ala Gly Lys Asp Gly Glu Ala Gly Ala Gln Gly Pro
545                 550                 555                 560

Pro Gly Pro Ala Gly Pro Ala Gly Glu Arg Gly Glu Gln Gly Pro Ala
            565                 570                 575

Gly Ser Pro Gly Phe Gln Gly Leu Pro Gly Pro Ala Gly Pro Pro Gly
        580                 585                 590

Glu Ala Gly Lys Pro Gly Glu Gln Gly Val Pro Gly Asp Leu Gly Ala
    595                 600                 605

Pro Gly Pro Ser Gly Pro Ala Gly Glu Pro Gly Pro Thr Gly Leu Pro
    610                 615                 620

Gly Pro Pro Gly Glu Arg Gly Gly Pro Gly Ser Arg Gly Phe Pro Gly
625                 630                 635                 640

Ala Asp Gly Val Ala Gly Pro Lys Gly Pro Ala Gly Glu Arg Gly Ser
            645                 650                 655

Pro Gly Pro Ala Gly Pro Lys Gly Ser Pro Gly Glu Ala Gly Arg Pro
        660                 665                 670

Gly Glu Ala Gly Leu Pro Gly Ala Lys Gly Leu Thr Gly Ser Pro Gly
    675                 680                 685

Ser Pro Gly Pro Asp Gly Lys Thr Gly Pro Pro Gly Pro Ala Gly Gln
    690                 695                 700

```
Asp Gly Arg Pro Gly Pro Pro Gly Pro Pro Gly Ala Arg Gly Gln Ala
705                 710                 715                 720

Gly Val Met Gly Phe Pro Gly Pro Lys Gly Ala Ala Gly Glu Pro Gly
                725                 730                 735

Lys Ala Gly Glu Arg Gly Val Pro Gly Pro Pro Gly Ala Val Gly Pro
            740                 745                 750

Ala Gly Lys Asp Gly Glu Ala Gly Ala Gln Gly Pro Pro Gly Pro Ala
        755                 760                 765

Gly Pro Ala Gly Glu Arg Gly Glu Gln Gly Pro Ala Gly Ser Pro Gly
    770                 775                 780

Phe Gln Gly Leu Pro Gly Pro Ala Gly Pro Pro Gly Glu Ala Gly Lys
785                 790                 795                 800

Pro Gly Glu Gln Gly Val Pro Gly Asp Leu Gly Ala Pro Gly Pro Ser
                805                 810                 815

Gly Pro Ala Gly Gly
            820

<210> SEQ ID NO 4
<211> LENGTH: 544
<212> TYPE: PRT
<213> ORGANISM: Artificial sequence
<220> FEATURE:
<223> OTHER INFORMATION: Hu-deam

<400> SEQUENCE: 4

Gly Ser Glu Gly Pro Glu Gly Val Arg Gly Glu Pro Gly Pro Pro Gly
1               5                   10                  15

Pro Ala Gly Ala Ala Gly Pro Ala Gly Asp Pro Gly Ala Asp Gly Glu
            20                  25                  30

Pro Gly Ala Lys Gly Ala Asp Gly Ala Pro Gly Ile Ala Gly Ala Pro
        35                  40                  45

Gly Phe Pro Gly Ala Arg Gly Pro Ser Gly Pro Glu Gly Pro Gly Gly
    50                  55                  60

Pro Pro Gly Pro Lys Gly Asp Ser Gly Glu Pro Gly Ala Pro Gly Ser
65                  70                  75                  80

Lys Gly Asp Thr Gly Ala Lys Gly Glu Pro Gly Pro Val Gly Val Glu
            85                  90                  95

Gly Pro Pro Gly Pro Ala Gly Glu Glu Gly Lys Pro Gly Ala Arg Gly
        100                 105                 110

Glu Pro Gly Pro Thr Gly Leu Pro Gly Pro Pro Gly Glu Arg Gly Gly
    115                 120                 125

Pro Gly Ser Arg Gly Phe Pro Gly Ala Asp Gly Val Ala Gly Pro Lys
130                 135                 140

Gly Pro Ala Gly Glu Arg Gly Ser Pro Gly Pro Ala Gly Pro Lys Gly
145                 150                 155                 160

Ser Pro Gly Glu Ala Gly Arg Pro Gly Glu Ala Gly Leu Pro Gly Ala
            165                 170                 175

Lys Gly Leu Thr Gly Ser Pro Gly Ser Pro Gly Pro Asp Gly Lys Thr
        180                 185                 190

Gly Pro Pro Gly Pro Ala Gly Glu Asp Gly Arg Pro Gly Pro Pro Gly
    195                 200                 205

Pro Pro Gly Ala Arg Gly Glu Ala Gly Val Met Gly Phe Pro Gly Pro
210                 215                 220

Lys Gly Ala Ala Gly Glu Pro Gly Lys Ala Gly Glu Arg Gly Val Pro
225                 230                 235                 240
```

-continued

```
Gly Pro Pro Gly Ala Val Gly Pro Ala Gly Lys Asp Gly Glu Ala Gly
            245             250             255
Ala Glu Gly Pro Pro Gly Pro Ala Gly Pro Ala Gly Glu Arg Gly Glu
            260             265             270
Glu Gly Pro Ala Gly Ser Pro Gly Phe Glu Gly Leu Pro Gly Pro Ala
            275             280             285
Gly Pro Pro Gly Glu Ala Gly Lys Pro Gly Glu Glu Gly Val Pro Gly
    290             295             300
Asp Leu Gly Ala Pro Gly Pro Ser Gly Ala Arg Gly Glu Pro Gly Phe
305             310             315             320
Pro Gly Glu Arg Gly Val Glu Gly Pro Pro Gly Pro Ala Gly Pro Pro
            325             330             335
Gly Ala Asp Gly Ala Pro Gly Asp Asp Gly Ala Lys Gly Asp Ala Gly
            340             345             350
Ala Pro Gly Ala Pro Gly Ser Glu Gly Ala Pro Gly Leu Glu Gly Met
            355             360             365
Pro Gly Glu Arg Gly Ala Ala Gly Leu Pro Gly Pro Lys Gly Asp Arg
    370             375             380
Gly Asp Ala Gly Pro Lys Gly Ala Asp Gly Ser Pro Gly Lys Asp Gly
385             390             395             400
Val Arg Gly Leu Thr Gly Pro Ile Gly Pro Pro Gly Pro Ala Gly Ala
            405             410             415
Pro Gly Asp Lys Gly Glu Ser Gly Pro Ser Gly Pro Ala Gly Pro Thr
            420             425             430
Gly Ala Arg Gly Ala Pro Gly Asp Arg Gly Glu Pro Gly Pro Pro Gly
            435             440             445
Pro Ala Gly Phe Ala Gly Pro Pro Gly Ala Asp Gly Glu Pro Gly Ala
    450             455             460
Lys Gly Glu Pro Gly Asp Ala Gly Ala Lys Gly Asp Ala Gly Pro Pro
465             470             475             480
Gly Pro Ala Gly Pro Ala Gly Pro Pro Gly Pro Ile Gly Asp Val Gly
            485             490             495
Ala Pro Gly Ala Lys Gly Ala Arg Gly Ser Ala Gly Pro Pro Gly Ala
            500             505             510
Thr Gly Phe Pro Gly Ala Ala Gly Arg Val Gly Pro Pro Gly Pro Ser
            515             520             525
Gly Asp Ala Gly Pro Pro Gly Pro Pro Gly Pro Ala Gly Lys Glu Gly
    530             535             540
```

USE OF RECOMBINANT GELATIN-LIKE PROTEINS AS PLASMA EXPANDERS AND COMPOSITIONS SUITABLE FOR PLASMA SUBSTITUTION

FIELD OF THE INVENTION

The invention relates to the use of recombinant gelatin-like proteins—or polypeptides—as plasma expanders and to compositions suitable for plasma substitution comprising such a plasma expander.

BACKGROUND OF THE INVENTION

A well established application of gelatin is the use as a colloid in solutions as substitutes for plasma. Such plasma substitutes can be used for controlling circulating blood volume in the management of shock resulting from for instance hemorrhages or burns. Care should be taken that the gelatin solution is made sterile, pyrogen and antigen free, and as the result of the average molecular size, is capable of maintaining a desired colloid osmotic pressure. In order to maintain a colloid osmotic pressure that is sufficient enough to have a sufficient amount of blood circulating and establish an efficient enough blood pressure over an adequate period of time, the average size of the gelatin molecules would be such that gelling becomes a problem.

To render gelatin suitable as a plasma expander, it has been chemically modified in such a way that gelability is drastically reduced. For this purpose it is known that gelatin can be simultaneously degraded and crosslinked, branched or inter-molecular bridges can be formed from the gelatin molecules. Probably the most successful modification is the preparation of succinylated gelatin as described in U.S. Pat. No. 2,827,419. A commercial preparation based on succinylated gelatin is currently available, known as Gelufusine®. The gelatin that is used is isolated from bovine origin and has an average molecular weight of 30,000. Other commercially available modified gelatines are Geloplasma® ('poligelatin') and Gelifundol® ('oxipoligelatin').

WO 01/34646 A2 describes recombinant gelatins structures of various molecular weights and various degrees of hydroxylation. A multitude of possible uses of the recombinant gelatins is claimed among which the use as a plasma expander. However, it does not provide information about which structures are adequate plasma expanders nor does it provide any specific recombinant gelatin in combination with its use as a plasma expander. Furthermore it is silent about methods to predictably control the duration of the oncotic effect of a plasma expander.

A disadvantage of the commercially used gelatin derivatives is that at least part of the administered gelatin leaves the circulatory system by transport over the blood vessel-wall by which their contribution to a stable clinical pattern is absent.

Another disadvantage of the commercially used gelatin derivatives is the fact that the gelatin used is isolated from animal sources such as animal bone and hide, in particular it is derived from bovine sources. Disadvantages of this material are the presence of impurities and the fact that the nature of the composition is not clearly defined and thus not reproducible. This may impose additional screening to ensure that the derivatisation process results in a product with the desired properties and may require careful purification steps. An additional problem nowadays, especially in relation to gelatin isolated from bovine sources, is the risk of contamination of the gelatin with factors responsible for the occurrence of Bovine Spongiform Encephalitis (BSE). For this reason the use of gelatin in blood substitution products may be prohibited. At present at least for one product, a modified gelatin of bovine origin, it is known that as a precautionary measure the product is no longer commercially available.

Another disadvantage of the commercially used gelatin derivatives is the fact that the preparation of the gelatin fragments with the intended size does not result in fully homogeneous material but in a heterogeneous mixture of gelatin fragments around a targeted average molecular weight. The smaller fragments will leave the blood circulation system by an early (unwanted) clearance (high clearance rate) by which their contribution to a stable clinical pattern is absent and the nephrotic system is negatively imposed.

Another disadvantage of the presently used gelatin derivatives as colloidal additives in plasma substitution compositions is the occurrence of hypersensitivity reactions in subjects. In particular subjects having an allergy or an auto-immune disease, or for some other reason having an increased level of antibodies, in particular IgE antibodies, are at risk. A case of acute emergency in which the administration of plasma expanders is required is in subjects suffering from shock, more specific hypoglycemic shock due to severe bleeding, excessive fluid loss or inadequate fluid uptake. In such a situation there is simply no time to assess possible risk factors, such as the presence of an allergy. If a subject is known to have an allergy, prophylactic administration of an antihistaminic can be contemplated. However, in case of acute emergency, any kind of prophylactic treatment is uncalled for. The condition of immediate hypersensitivity, which can occur upon application of the presently used gelatin derivatives, is known as anaphylactic shock. This is a life-threatening condition where blood pressure is too low to sustain life, which in fact was the condition that should be counteracted by the plasma expander. Since a subject receiving the plasma expanders already suffers an acute trauma the condition of anaphylactic shock is most likely to be fatal.

SUMMARY OF THE INVENTION

It is an object of the invention to provide alternative compositions suitable as plasma substitution comprising a plasma expander, which will have a lower clearance rate from blood circulation.

It is also an object of the invention to provide alternative compositions suitable as a plasma substitution comprising a plasma expander that provides better and predictable regulation of clearance rate Another object of the invention is to provide alternative compositions suitable as a plasma substitution comprising a plasma expander that is less susceptible to proteolytic degradation Furthermore it is an object of the invention to provide alternative compositions suitable as plasma substitution comprising a plasma expander that will reduce the occurrence of immunological reactions, in particular anaphylactic shock.

Surprisingly it has been found that recombinant gelatin-like proteins with a molecular weight from at least 10,000 Daltons to 25,000 Daltons or to at most 50,000 Daltons, which have an isoelectric point of less than 8 have a lower clearance rate than conventional gelatins. In the context of this invention such a gelatin-like protein is called a monomer or monomeric unit. By recombinant methods gelatin-like proteins build up of repeats of this monomer or monomeric unit can be prepared. In the context of this invention such a gelatin-like protein is called a multimer or polymer or, in particular a dimer, trimer or tetramer.

Further it was surprisingly found that increasing the number of repetitions of the monomeric unit in a polymer results in a gradually decreasing clearance rate. Surprisingly it was also found that an increase of the charge density of the gelatin-like protein by replacement of Gln by Glu or Asn by Asp decreases the clearance rate and the oncotic effect.

Further it was surprisingly found that recombinant gelatin-like proteins that are in essence free of hydroxyproline do not give rise to an immunological reaction with blood samples containing IgE antibodies.

Thus, compositions according to the invention comprise a solution of saline in a physiologically acceptable concentration and a protein having a colloid osmotic function characterized in that the compound having a protein colloid osmotic function is a recombinant gelatin-like protein with an isoelectric point of less than 8 and a molecular weight from at least 10,000 Daltons to 25,000 Daltons or at most 50,000 Daltons. In a further aspect the invention concerns a dimer or a trimer or a tetramer of a recombinant gelatin-like protein with an isoelectric point of less than 8 and a molecular weight from at least 10,000 Daltons to 25,000 Daltons, or at most 50,000 Daltons.

The invention relates also to the use as a plasma expander of a monomer or dimer or trimer or tetramer or any other multimer of a recombinant gelatin-like protein with an isoelectric point of less than 8 and a molecular weight from at least 10,000 Daltons to 25,000 or at most 50,000 Daltons.

Description of the Sequences
SEQ ID NO 1: Hu-1
SEQ ID NO 2: Hu-3 (trimer of Hu-1)
SEQ ID NO 3: Hu-4 (tetramer of Hu-1)
SEQ ID NO 4: Hu-deam

Figure 1:
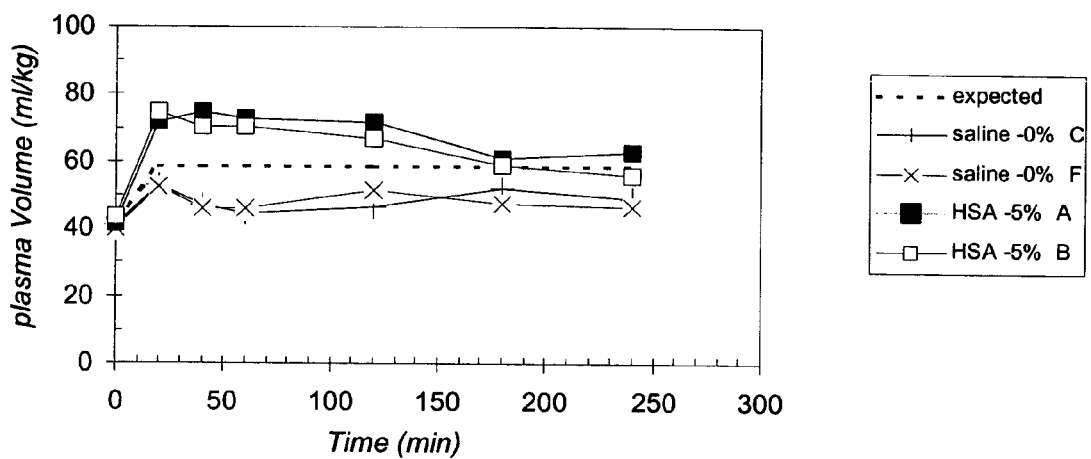
FIG. 1. Plasma volume expansion as a function of time after infusion of saline and HSA.

In all figures time in minutes is plotted against plasma volume in ml/kg.

DESCRIPTION OF THE INVENTION

According to the invention a composition is provided comprising as a compound having a colloid osmotic function a monomer or dimer or trimer or tetramer or multimer of a recombinant gelatin-like protein with an isoelectric point of less than 8 and the monomer has a molecular weight from at least 10,000 Daltons to 25,000 Daltons or at most 50,000 Daltons. Preferably the monomer has a molecular weight of 10,000 to at most 25,000, more preferably of 15,000 to at most 25,000, even more preferably to at most 20,000.

Recombinant production of gelatin-like proteins in particular in a micro-organism allows reproducible production of proteins of constant composition without the risk of prion related health hazards.

In example 2 it is shown that compositions according to the invention have a lower clearance rate than commercially available compositions. Furthermore it is shown that the clearance rate unexpectedly decreases with the number of repetitions of recombinant gelatin monomers according to the invention in a polymer. The component of the total osmotic pressure due to colloids is known as colloid osmotic pressure or as oncotic pressure. There is a clear hyperoncotic effect for compositions according to the invention, however, the hyperoncotic effect for recombinant gelatin-like molecules only differing in molecular weight is longer lasting upon increase in the molecular weight showing that the molecular weight can be applied to steer the time span of the hyperoncotic effect. This remarkable effect is of high practical relevance for the clinical practice, for which a well controlled duration of the oncotic effect has been searched for in the past.

In example 3 it is shown that in the case of two blood samples out of a panel of 60 samples obtained from subjects in which IgE antibodies in the samples are present, two tested commercial preparations display specific binding of the IgE to the gelatin derivative, whereas in all the samples the compositions according to the invention display no risk of a hypersensitivity reaction. If the subjects from which the two positively tested samples originated, when in need, were to receive the commercially available gelatin based plasma substitution compositions, said subjects would likely suffer anaphylactic shock.

A natural gelatin molecule in its primary amino acid sequence basically consists of repeats of Gly-Xaa-Yaa triplets, thus approximately one third of the total number of amino acids is a glycine. The molecular weight of gelatin is typically large, values of the molecular weight vary from 10,000 to 300,000 daltons. The main fraction of natural gelatin molecules has a molecular weight around 90,000 daltons. The average molecular weight is higher than 90,000 daltons.

Furthermore, characteristic for gelatin is the unusual high content of proline residues. Even more characteristic is that in natural gelatin a number of the proline residues is hydroxylated. Most prominent site of hydroxylation is the 4-position resulting in the presence in the gelatin molecule of the unusual amino acid 4-hydroxyproline. In a triplet 4-hydroxyproline is always found in the Yaa position. Very few proline residues are hydroxylated at the 3 position. In contrast with 4-hydroxyproline, 3-hydroxyproline is always found at the carboxyl side of a glycine residue, thus in the Xaa position in a triplet. Different enzymes are responsible for the formation of 3- or 4-hydroxyproline.

Based on known amino acid compositions, it is estimated that in a gelatin molecule derived from a mammal, approximately 22% of the amino acids are a proline or a hydroxyproline residue. However lower contents of proline and hydroxyproline are found in fish, in particular cold water fish. A rough estimate is that proline and hydroxyproline residues are present in approximately equal amounts, thus in a gelatin molecule derived from a mammal approximately 11% of the amino acids are prolines and approximately 11% are hydroxyprolines. As substantially all hydroxyproline is found in the Yaa position, it is estimated that approximately one third of all triplets in a gelatin molecule comprise a hydroxyproline. The presence of the hydroxyproline residues is responsible for the fact that a gelatin molecule in its secondary structure can adopt a helical conformation.

Furthermore, another amino acid present in natural gelatin that is found in very few other proteins is 5-hydroxylysine. Lysine residues modified in this way are always found in the Yaa position in a triplet.

Gelatin-like proteins for use according to the invention are understood as proteins in which at least 5% of the total number of amino acids is a proline residue. By this percentage the gelatin-like characteristics, for the purpose of this invention not being defined as the gelling property but as the absence of unpreferred 3-dimensional globular domains, is assured. Preferably in the gelatin-like protein at least 10%, more preferably at least 15% of the total number of amino acids is a proline residue. The lower the proline content of a protein the more the distribution of the proline residues in the protein becomes relevant. Thus in a protein in which 5% of the total number of amino acids is a proline residue, these residues are preferably evenly distributed. In designing a suitable protein the skilled person, for instance with the aid of computer modeling systems, will be able to design sequences comprising proline residues which will not give rise to globular domains. In order to prevent the formation of globular domains as a guideline the gelatin-like protein for use in the invention preferably should not comprise stretches of more than 20 amino acids without a proline residue.

A predominant feature of gelatins is the presence of Gly-Xaa-Yaa triplets. Such triplets are preferably also present in the gelatin-like proteins used in the invention. It is however possible to design a protein in which Gly-Xaa-Yaa triplets or stretches of Gly-Xaa-Yaa triplets are separated by one or more amino acids. In such a gelatin-like protein having 'interrupted' triplets or stretches of triplets the definition of gelatin-like characteristics given above is useful. In relation to a protein consisting completely of Gly-Xaa-Yaa triplets the definition given above of a gelatin-like protein for use in the invention can be described as a protein in which at least 15% of the triplets comprise a proline residue. Preferably such a gelatin-like protein does not comprise a stretch of more than 6 triplets without a proline residue. It is preferred a gelatin-like protein for use in the invention comprises stretches of at least 10, preferably at least 20, more preferably more than 30 consecutive repeats of Gly-Xaa-Yaa triplets.

In order to maintain a suitable colloid osmotic pressure in combination with a targeted clearance rate from the blood circulation system when administered to a subject, the molecular weight of a gelatin-like molecule for use according to the invention should be at least 10,000 Daltons, preferably more than 20,000 Daltons, more preferably more than 30,000 Daltons. Even more preferably the molecular weight is between about 30,000 Daltons and 120,000 Daltons. To reach molecular weights of more than 50,000 Daltons a multimer, at least a dimer, of the gelatin-like protein having a colloid osmotic function, being a recombinant gelatin-like protein with a molecular weight of from at least 10,000 Daltons to at most 50,000 Daltons and having an isoelectric point of less than 8, can be prepared. Preferably, the gelatin-like molecule for use according to the invention has a low amount of hydroxyproline residues, meaning that less than 10% of the aminoacid residues in the polypeptide are hydroxyproline residues. The amount of hydroxyprolines is restricted to prevent gelation of the recombinant gelatin. It is preferred to avoid gelation, since this limits the concentration in which the plasma expander can be applied or requires warming of the plasma expander solution before administering.

The amount of hydroxyprolines can be determined by any standard amino acid analysis method like, for example, described in HP AminoQuant Series II, operators handbook, 1990, Hewlett-Packard GmbH, Federal Republic of Germany, Waldbronn Analytical Division, HP Part No. 01090-90025.

There are subjects, like those having allergies or auto-immune diseases, that cannot tolerate the commercial preparations for plasma substitution based on gelatin derivatives. Faced with this problem a first improvement could be to try to improve on the purification of the gelatin proteins. One approach is optimizing even further the isolation procedure of natural gelatin or optimizing the derivatization and subsequent purification procedure. Another possibility could lie in alternative sources or alternative production methods for gelatin. Having knowledge of the current biotechnological developments and the advance that is made with respect to recombinant production of gelatins and collagens it could be contemplated to follow such a route for reproducible production of proteins of constant composition.

As mentioned earlier, plasma substitution compositions comprising gelatins can be lethal to subjects having an allergy or an auto-immune disease. When pursuing the approach of recombinant production of gelatins and bearing in mind that such gelatins should be even less immunogenic in human subjects than the presently used bovine derived gelatins, it is obvious to take up production of recombinant human gelatin. In addition it is obvious not to induce marked changes in the basic gelatin structure.

Preferably, in one embodiment the recombinant gelatin-like proteins contains less than 10% hydroxyprolines. The presence of hydroxyproline residues in natural gelatin allows the molecule to adopt a helical conformation. A reduced amount of hydroxyproline residues prevents the gelatin-like proteins from adopting such a conformation and prevents the gelatin-like molecule from gelling, even at low temperatures.

There is no prior art information on immunological or antigenic properties of gelatin-like proteins useful in the invention. The distinctiveness of the gelatin-like proteins for use according to the invention from natural gelatin, both chemically and conformationally, would dissuade the use of such a protein in plasma substitution compositions. Surprisingly however, gelatin-like proteins for use according to the invention show no immunogenic interaction with blood having increased amounts of IgE antibodies.

The gelatin-like protein can be made de novo from a synthetic nucleic acid sequence. This allows tailor-made design of the protein. The designed synthetic nucleic acid sequence can be expressed in suitable micro-organisms using known recombinant techniques.

With respect to the design of gelatin-like proteins for use in the invention, several properties of the proteins are addressed. For instance the clearance speed of the gelatin-like proteins can be "designed-in" by the choice for a specific size or a specific range of sizes of the gelatin-like proteins. In particular this could be advantageous in combination with known nephrotic system characteristics (measured by for instance the creatinine clearance pattern) of subjects to whom the gelatin-like proteins are administered. The size of the gelatin-like protein can be designed by multimerisation of a specific monomer (which can also be regarded as a block polymer), representing for instance a specific part of a native human collagen. A series of plasma expanders, each of them with a well defined clearance characteristic can be designed by step by step increase of the number of monomers in the multimeric, complete plasma expanders, consisting of one, two, three, four and more monomers of a gelatin-like protein. The monomer amino acid (AA) sequence can be chosen from the human collagen sequence, by selecting an AA domain with a low iso-electric point (IEP) of the polypeptide and a low sensitivity to any proteolytic activity, which could be present in the unicellular production system of interest for example, yeast, fungi and others. The size of the gelatin-like proteins is further of importance for the colloid osmotic pressure, as discussed herein, it exercises. Yet further the iso-electric point (IEP) and number of aminoacids with an ionizable residual group can be tuned by the composition of acidic and basic amino acid residues in the gelatin-like proteins.

Recombinant gelatin-like proteins according to the invention have an isoelectric point of less than 8. At pH 8 lysine and arginine are positively charged, glutamic acid and aspartic acid are negatively charged and glutamine and asparagine are neutral. Glutamine and asparagine can be replaced by their acids by point mutations in the expressed sequences or by deamidation of the recombinant structures after expression. Negatively charged groups like aspartic- or glutamic acid residues should be preferably randomly distributed over the recombinant gelatin-like protein. When desirable an increased number of aminoacids with negatively charged residual groups can be designed in, as long as this does not result in an increased antigenicity.

Important to this invention is that a recombinant gelatin-like protein is selected or designed having a proper isoelectric point, surprisingly decreasing the clearance rate from blood circulation. By preparing a multimer of such a recombinant gelatin-like protein this effect is even improved, while maintaining the desired isoelectric point. The isoelectric point is less than 8, preferably less than 7, more preferably less than 6 even more preferably less than 5. More preferably the isoelectric point of the gelatin-like protein is at least more than 3, more preferably more than 4. Preferred ranges according to the invention are therefore gelatin-like proteins having an isoelectric point of (at least) to (at most): 3–8, 4–8, 3–7, 4–7, 3–6, 4–6, 3–5 and 4–5.

In one embodiment the amount of negatively charged groups at pH lower than 8 is increased by deamidation of asparagine and/or glutamine to yield aspartic acid and/or glutamic acid.

In one embodiment the composition according to the invention comprises a gelatin-like protein which is homo-diperse in nature. Homodisperse means of single composition and molecular weight. Variations in composition that can occur due to the recombinant production process are allowed. In terms of molecular weight a useful definition of homodispersity would be that at least 75% of the total amount of gelatin-like protein in the composition has a molecular weight that lies within a rage of plus or minus 10% around a selected molecular weight. The selected molecular weight depends on the desired colloid osmotic pressure and on the desired clearance rate from the blood circulation system. In another embodiment the composition according to the invention comprises two or more gelatin-like proteins each being homodiperse in nature but with different molecular weights. The difference in molecular weight results in a different clearance pattern from the circulating blood. Such a composition allows tuning of the plasma expanding activity of the composition over prolonged periods of time.

The starting point for the gelatin-like protein for use in the invention can also be an isolated gene encoding a naturally occurring gelatin molecule, which is processed further by recombinant means. Preferably the gelatin-like protein used according to the invention resembles a human native amino acid sequence preferably with this difference that less than 10% of the aminoacid residues are hydroxyproline residues.

The gelatin-like proteins used according to the invention resemble a human native amino acid sequence when they contain less than 1% point mutations wherein replacement of asparagine by aspartic acid and glutamine by glutamic acid are not considered as point mutations.

The gelatin-like proteins for use according to the invention can be produced by recombinant methods as disclosed in van Heerde et al. U.S. Pat. No. 6,051,081 ("U.S. Pat. No. 6,051,081") or WO01/34646. Also for enablement of the production and purification of gelatin-like proteins that can be suitably used in composition according to the invention reference is made to the examples in U.S. Pat. No. 6,051,081. Thus the gelatin-like proteins can be produced by expression of nucleic acid sequence encoding such polypeptide by a suitable micro-organism. The process can suitably be carried out with a fungal cell or a yeast cell. Suitably the host cell is a high expression host cells like *Hansenula*, *Trichoderma*, *Aspergillus*, *Penicillium*, *Neurospora* or *Pichia*. Fungal and yeast cells are preferred to bacteria as they are less susceptible to improper expression of repetitive sequences. Most preferably the host will not have a high level of proteases that attack the collagen structure expressed. In this respect *Pichia* or *Hansenula* offers an example of a very suitable expression system. Use of *Pichia pastoris* as an expression system is disclosed in U.S. Pat No. 6.051,081. Preferably the micro-organism is free of active post-translational processing mechanism such as in particular hydroxylation of proline and also hydroxylation of lysine. The host to be used does not require the presence of a gene for expression of prolyl-4-hydroxylase. Preferably the host also does not require the presence of lysyl-hydroxylase. The selection of a suitable host cell from known industrial enzyme producing fungal host cells specifically yeast cells on the basis of the required parameters described herein rendering the host cell suitable for expression of recombinant gelatin-like proteins suitable in compositions according to the invention in combination with knowledge regarding the host cells and the sequence to be expressed will be possible by a person skilled in the art.

With the currently available molecular biotechnological techniques multimers up to and including the tetramer have been prepared. The invention also encompasses multimers with repeats of a monomeric unit of more than four, e.g. five, six, seven, eight, nine, ten and more.

When produced by recombinant means, especially by expression of recombinant genes in yeasts, the proteins for use according to the invention preferably do not contain cysteine or another mercapto amino acid, nor do they contain a combination of methionine and arginine in 1–4 position (Met-Xay-Xaz-Arg), as such a sequence is sensitive to enzymatic proteolysis. The skilled person will be aware of other possible sites, i.e. specific stretches of amino acids, susceptible to proteolysis when designing or selecting an amino acid sequence according to this invention and will avoid including such sites in the recombinant gelatin-like protein.

It may be noted that the proteins for use according to the invention can also be partly or wholly produced by methods other than DNA expression, e.g. by chemical protein synthesis; in that case, they may also contain non-natural amino acids.

In order to obtain the composition of the invention the gelatin-like protein is dissolved in saline in a physiologically acceptable concentration at physiological pH. Saline is a solution of $Na^+$ and $Cl^-$ ions in water. Since it is highly likely that plasma substitution compositions are administered in great volumina, care should be taken that dilution effects do not disturb electrolyte balances. When preparing compositions according to the invention the skilled person will be able to apply appropriate concentrations of $Na^+$ and $Cl^-$ ions. Workable margins would be 120–170 mmol/l for $Na^+$ and 90–140 mmol/l for $Cl^-$. If so desired the composition according to the invention could comprise one or more additional components normally found in blood. For instance a composition according the invention comprises one or more components in a physiologically acceptable concentration selected from $Mg^{2+}$, $K^+$, $Ca^{2+}$, $HPO_4^{2-}$, $H_2PO_4^-$ and glucose. The skilled person will be able to determine what is a physiologically acceptable concentration for each component. Suitably, a composition according to the invention also comprises a buffering compound, preferably selected from the group consisting of $HCO_3^-$ and lactate. The skilled person will be able to determine the appropriate amount of buffer in order to maintain the composition at a physiologically acceptable pH.

It is preferred the composition according to the invention is approximately isotonic or iso-osmotic with blood of human subjects, therefore the composition has an osmolarity preferably in the range from 270–300 mOsm.

The purpose of the gelatin-like proteins is to maintain an appropriate colloid osmotic pressure in order to keep a sufficient amount of blood volume circulating. The non-gelling property of the proteins for use according to one embodiment of the invention has the advantage that macromolecules of considerable size can be used which will not be rapidly cleared from the system. In order to be effective as plasma expander the gelatin-like monomer should have a molecular weight of at least 10,000 Daltons, but not higher than 50,000. Preferably the monomer has a molecular weight of 10,000 to at most 25,000, more preferably of 15,000 to at most 25,000, even more preferably to at most 20,000.

According to the invention it is possible to apply much larger gelatin-like proteins by multimerisation of the monomer unit, in case this is preferred depending on the desired colloid osmotic pressure and/or the desired clearance rate from the blood circulation system. Compositions comprising gelatin-like proteins of high molecular weight can be applied without the risk of gelling or of a too high viscosity in case the hydroxylation of proline (Pro) is reduced if compared to traditional gelatins. It does not seem likely however, that gelatin-like proteins having a molecular weight of higher than 200,000 Daltons can be suitably applied in compositions according to the invention. Molecular weights of higher than 100,000 Daltons are not preferred, but were up to now limited because of their high hydroxyproline content which causes gelation.

Gelatin-like proteins according to the invention have an isoelectric point that is lower than the pH of human blood, which is around pH 8. Preferably the isoelectric point of the gelatin-like protein is at least about 4 and at most about 7.

Commercial and free software is available to the skilled person to design gelatin-like proteins that can be used and are suitable in compositions according to this invention. Isoelectric point of structures with known aminoacid sequence can be calculated by, for example, JaMBW 1.1, a program of L. I. G. Toldo of the Molecular Biology Laboratory of Heidelberg.

In one embodiment in the compositions and in the use according to the invention the number of negatively charged aminoacid residues at pH 8 in the recombinant gelatin-like protein, minus the number of positively charged aminoacid residues at pH 8 in the recombinant gelatin-like protein is at least 2, preferably at least 3.

Many blood plasma proteins have a transport function. Low isoelectric point reduces the chance that the gelatin-like protein interacts with these blood plasma proteins and thereby the chance that the blood plasma proteins function is hindered.

A possible explanation for the lower clearance rate of the gelatin-like proteins according to the invention is the nature of the glycocalyx barrier that lines the walls of blood vessels. This glycocalyx regulates the transport of substances like solutes and proteins between blood vessels and the surrounding tissue. The exact functions of the glycocalyx and the mechanisms by which such functions are performed have not been elucidated. Interaction between glycocalyx and foreign proteins like gelatins from plasma expander are therefore better avoided. Gelatin-like proteins according to the invention have less interaction with the glycocalyx which serves to reduce the transport of gelatin-like proteins from the blood to the surrounding tissue. An increase of the total surplus of negative charge of the gelatin-like plasma expander at pH 8, by for instance replacing Gln by Glu or Asn by Asp is a method to decrease the interaction between the plasma expander and the glycocalyx further and to increase the intravascular half life time of the plasma expander. Also (temporary) damage of the glycocalyx by gelatin-like proteins according to the invention is prevented by repulsion of said gelatin-like proteins by the glycocalyx. Such (temporary) damage would increase the circulating blood volume containing plasma expander, resulting in an undesired decrease in blood pressure.

The composition of the invention comprises an amount of gelatin-like proteins which exerts an osmotic pressure comparable to or slightly exceeding the osmotic pressure exerted by human serum albumin in blood. Determining the colloid osmotic pressure of a composition is a routine measurement for the skilled person, for instance by using a commercially available membrane osmometer equipped with a suitable semi-permeable membrane, for instance with a cut-off of 20,000 Daltons. The skilled person will be able to determine the correct amount of gelatin-like protein suited for the desired osmotic pressure. Usually the amount of gelatin-like protein that can be applied lies in the range from 2–8 weight %.

If so desired, it is possible to introduce simultaneously with the plasma substitution composition of the invention a pharmacologically active compound. For instance it may be advantageous to simultaneously introduce medicaments involved in the blood clotting process. In particular such a composition could be of use in the application of a plasma expander during surgery or preoperative dilution of blood. Thus in another embodiment the composition according to the invention comprises a pharmacologically active compound.

Making use of the advantageous property of the gelatin-like protein that it has a s sustained circulation time in plasma it is particularly envisaged to covalently attach pharmaceutically active compounds to the gelatin-like protein. In a further embodiment the composition according to the invention comprises a pharmaceutically active compound which is covalently attached to the gelatin-like protein.

Covalent attachment of a pharmaceutically active compound to a protein is routine practice for an ordinary skilled organic chemist. For instance coupling of a carboxyl function in a drug to an amino group of a lysine in a protein can be achieved by converting the carboxyl group in its activated ester using DCC, or EDC, and NHS, which reacts with the free amine.

As in a protein lysine residues are the residues of choice for the covalent attachment of other molecules, it is for this purpose not desired to have a protein that is in essence free of lysine residues. In contrast, lysine residues should be present and preferably the number of lysine residues present is known, for this allows an estimation of how many pharmacologically active compounds are coupled to a protein and thus allows appropriate dosage of the medicament. The design of synthetic nucleic acid sequences de novo now offers the advantageous possibility to introduce a specific amount of lysine residues and thus the production of well defined gelatin-like proteins bearing pharmaceutically active compounds. A distinct correlation between clearance time of the protein and dosage of the medicament can be made.

After administration the coupled medicament will not diffuse from the circulating blood into the interstitium. This is a specific advantage for medicaments which should function intravascularly. Unwanted side effects by diffusion of the medicament into the interstitial fluid throughout a subject are avoided. Also medicaments having an intravascular as well as an extravascular activity profile could benefit from the focus on the intravascular mode of action.

Clearance by liver and kidney will be kept to a minimum ensuring a more constant plasma level of the medicament. Half-lives of medicaments coupled to gelatin-like proteins will be increased.

Examples of medicaments which are administered intravascularly and which are suitable for coupling to the protein used in the invention are medicaments involved in intervening blood clotting, vasodilatation, function of erythrocytes, thrombocytes and leukocytes, thrombosis, immuneresponses, blood levels of messenger molecules such as hormones Specific examples are heparin, beta-blockers, blood pressure regulators such as angiotensin antagonists and antibiotics.

It should be understood that modification of the gelatin-like proteins for use in compositions according to the invention is not restricted to the coupling of pharmacologically active compounds. To improve the properties other modifications after the gelatin-like protein has been recombinantly produced and isolated are possible. For instance modifications to influence the iso-electric point or the solubility or another relevant property can be advantageous. Care should be taken that such a modification does not introduce elements that are likely to induce an immunogenic or antigenic reaction.

EXAMPLES

Example 1

Human recombinant gelatin-like polypeptides Hu-1 (SEQ ID NO: 1), Hu-3 (SEQ ID NO: 2), Hu-4 (SEQ ID NO: 3) and Hu-deam (SEQ ID NO: 4) was produced by recombinant methods as disclosed in U.S. Pat. No. 6,150,081.

The encoded amino acid sequence of the mature (processed) Hu-1 is as follows (SEQ ID NO: 1):

```
  1G P P G E P G P T G L P G P P G E R G G P G S R G F P G A D
 31G V A G P K G P A G E R G S P G P A G P K G S P G E A G R P
 61G E A G L P G A K G L T G S P G S P G P D G K T G P P G P A
 91G Q D G R P G P P G P P G A R G Q A G V M G F P G P K G A A
121G E P G K A G E R G V P G P P G A V G P A G K D G E A G A Q
151G P P G P A G P A G E R G E Q G P A G S P G F Q G L P G P A
181G P P G E A G K P G E Q G V P G D L G A P G P S G P A G G
```

Molecular weight: 18.4 kDa, isoelectric point: 5.35.

In a similar way Hu-3 (SEQ ID NO: 2), a trimer of Hu-1 was produced:

```
  1G P P G E P G P T G L P G P P G E R G G P G S R G F P G A D
 31G V A G P K G P A G E R G S P G P A G P K G S P G E A G R P
 61G E A G L P G A K G L T G S P G S P G P D G K T G P P G P A
 91G Q D G R P G P P G P P G A R G Q A G V M G F P G P K G A A
121G E P G K A G E R G V P G P P G A V G P A G K D G E A G A Q
151G P P G P A G P A G E R G E Q G P A G S P G F Q G L P G P A
181G P P G E A G K P G E Q G V P G D L G A P G P S G P A G E P
211G P T G L P G P P G E R G G P G S R G F P G A D G V A G P K
241G P A G E R G S P G P A G P K G S P G E A G R P G E A G L P
271G A K G L T G S P G S P G P D G K T G P P G P A G Q D G R P
```

```
-continued
301G P P G P P G A R G Q A G V M G F P G P K G A A G E P G K A

331G E R G V P G P P G A V G P A G K D G E A G A Q G P P G P A

361G P A G E R G E Q G P A G S P G F Q G L P G P A G P P G E A

391G K P G E Q G V P G D L G A P G P S G P A G E P G P T G L P

421G P P G E R G G P G S R G F P G A D G V A G P K G P A G E R

451G S P G P A G P K G S P G E A G R P G E A G L P G A K G L T

481G S P G S P G P D G K T G P P G P A G Q D G R P G P P G P P

511G A R G Q A G V M G F P G P K G A A G E P G K A G E R G V P

541G P P G A V G P A G K D G E A G A Q G P P G P A G P A G E R

571G E Q G P A G S P G F Q G L P G P A G P P G E A G K P G E Q

601G V P G D L G A P G P S G P A G G
```

In a similar way Hu-4 (SEQ ID NO: 3), a tetramer of Hu-1 was produced:

```
  1G P P G E P G P T G L P G P P G E R G G P G S R G F P G A D

31G V A G P K G P A G E R G S P G P A G P K G S P G E A G R P

61G E A G L P G A K G L T G S P G S P G P D G K T G P P G P A

91G Q D G R P G P P G P P G A R G Q A G V M G F P G P K G A A

121G E P G K A G E R G V P G P P G A V G P A G K D G E A G A Q

151G P P G P A G P A G E R G E Q G P A G S P G F Q G L P G P A

181G P P G E A G K P G E Q G V P G D L G A P G P S G P A G E P

211G P T G L P G P P G E R G G P G S R G F P G A D G V A G P K

241G P A G E R G S P G P A G P K G S P G E A G R P G E A G L P

271G A K G L T G S P G S P G P D G K T G P P G P A G Q D G R P

301G P P G P P G A R G Q A G V M G F P G P K G A A G E P G K A

331G E R G V P G P P G A V G P A G K D G E A G A Q G P P G P A

361G P A G E R G E Q G P A G S P G F Q G L P G P A G P P G E A

391G K P G E Q G V P G D L G A P G P S G P A G E P G P T G L P

421G P P G E R G G P G S R G F P G A D G V A G P K G P A G E R

451G S P G P A G P K G S P G E A G R P G E A G L P G A K G L T

481G S P G S P G P D G K T G P P G P A G Q D G R P G P P G P P

511G A R G Q A G V M G F P G P K G A A G E P G K A G E R G V P

541G P P G A V G P A G K D G E A G A Q G P P G P A G P A G E R

571G E Q G P A G S P G F Q G L P G P A G P P G E A G K P G E Q

601G V P G D L G A P G P S G P A G E P G P T G L P G P P G E R

631G G P G S R G F P G A D G V A G P K G P A G E R G S P G P A

661G P K G S P G E A G R P G E A G L P G A K G L T G S P G S P

691G P D G K T G P P G P A G Q D G R P G P P G P P G A R G Q A

721G V M G F P G P K G A A G E P G K A G E R G V P G P P G A V
```

-continued
```
751G P A G K D G E A G A Q G P P G P A G P A G E R G E Q G P A

781G S P G F Q G L P G P A G P P G E A G K P G E Q G V P G D L

811G A P G P S G P A G G
```

In a similar way Hu-deam (SEQ ID NO: 4) was made in which glutamine residues were replaced by glutamic acid residues and asparagine residues were replaced by aspartic acid residues thus reducing the isoelectric point from 8.7 to 4.6.

```
  1G S E G P E G V R G E P G P P G P A G A A G P A G D P G A D

31G E P G A K G A D G A P G I A G A P G F P G A R G P S G P E

61G P G G P P G P K G D S G E P G A P G S K G D T G A K G E P

91G P V G V E G P P G P A G E E G K P G A R G E P G P T G L P

121G P P G E R G G P G S R G F P G A D G V A G P K G P A G E R

151G S P G P A G P K G S P G E A G R P G E A G L P G A K G L T

181G S P G S P G P D G K T G P P G P A G E D G R P G P P G P P

211G A R G E A G V M G F P G P K G A A G E P G K A G E R G V P

241G P P G A V G P A G K D G E A G A E G P P G P A G P A G E R

271G E E G P A G S P G F E G L P G P A G P P G E A G K P G E E

301G V P G D L G A P G P S G A R G E P G F P G E R G V E G P P

331G P A G P P G A D G A P G D D G A K G D A G A P G A P G S E

361G A P G L E G M P G E R G A A G L P G P K G D R G D A G P K

391G A D G S P G K D G V R G L T G P I G P P G P A G A P G D K

421G E S G P S G P A G P T G A R G A P G D R G E P G P P G P A

451G F A G P P G A D G E P G A K G E P G D A G A K G D A G P P

481G P A G P A G P P G P I G D V G A P G A K G A R G S A G P P

511G A T G F P G A A G R V G P P G P S G D A G P P G P P G P A

541G K E G
```

In positions 108, 318 and 336 an arginine has been replaced by a proline in order to prevent proteolysis.

Example 2

Pre-Clinical Evaluation of Gelatin Solutions in Rats

Filling of the vascular system is related to the oncotic activity in vivo. The oncotic activity can be determined by studying the plasma volume increase by a certain dose of gelatin. In practice, to obtain good measurable effects, for example, 20 ml/kg bodyweight (about 30% of the blood volume) can be withdrawn and replaced by the same volume of solution with a certain concentration of gelatin (around the estimated iso-oncotic concentration). The in vivo oncotic effect of a certain dose of gelatin solution can be determined by comparing the actual effects on the red blood cell count with the expected effects.

When the macromolecules are cleared from the circulation the plasma volume will decrease, leading to an increase in red blood cell count or hematocryt. Therefore, measuring the changes in the red blood cell count will reveal the duration of the oncotic. Relatively small macromolecules (<30 kD, depending on charge and shape) may be cleared by the kidneys. Kidney excretion can be determined by collecting urine and measuring the gelatin concentration. When large amounts of gelatin are excreted, kidney tubuli may become blocked by precipitation of gelatin in kidney tubuli. This can be studied by light microscopy.

Constituents of the gelatin solutions, especially impurities from yeast, may induce inflammatory responses. This may, amongst others, lead to vasoactivity and/or activation of neutrophils.

Because the half-life is in the order of magnitude of hours, a 4 hour duration seems to be sufficient for initial experiments. This means that the whole experiment can be done under anesthesia, which facilitates blood pressure measurement and blood sampling and minimizes discomfort for the rats.

The iso-oncotic activity can be determined without measuring plasma concentrations, but for determination of the clearance an assay for measuring gelatin in plasma and urine should be available. Alternatively, labeled gelatin could be used, with the drawback that labeling may change the properties.

Protocol:

Animal Data
 Species: Rat
 Strain/Sex: Wistar HsdCpb:WU, female

Procedures
 1. Administration of test solutions
 Withdrawal of blood: 20 ml/kg in 10 minutes
 Infusion of gelatin solution: 20 ml/kg (4–6 ml) in 10 minutes
 2. Blood samples Blood: 0.2 to 1.5 ml blood samples were collected from the venous cannula into syringe and rapidly transferred into EDTA-containing polypropylene vials at t=0, 60, 120 and 240 min.
 3. Duration of the experiment
 The experiments were terminated 240 minutes after administration of the test solution by giving a lethal dose of pentobarbital.

| TEST/CONTROL/COMPARISON SOLUTIONS | |
|---|---|
| Test solution 1 | recombinant human gelatin, 55.2 kD Hu-3 |
| identity | Hu-3, 55.2 kD |
| supplier | Fuji |
| formulation | freeze dried |
| remarks | reconstituted with 0.9% NaCl at 4 g/100 ml and stored at 4oC until adminstration (for less than 1 week) |
| Test solution 2 | recombinant human gelatin, 73.6 kD Hu-4 |
| identity | Hu-4 73.6 kD |
| supplier | Fuji |
| formulation | freeze dried |
| remarks | reconstituted with 0.9% NaCl at 4 g/100 ml and stored at 4oC until adminstration (for less than 1 week) |
| Test solution 3 | recombinant human gelatin. deamidated, 48 kD Hu-deam |
| identity | Hu-deam |
| supplier | Fuji |
| formulation | freeze dried |
| remarks | reconstituted with 0.9% NaCl at 4 g/100 ml and stored at 4oC until adminstration (for less than 1 week) |
| Control solution | saline |
| identity | 0.9% (w/v) NaCl |
| supplier | NPBI, Emmer-Compascuum, The Netherlands |
| formulation | sterile fluid for iv administration |
| remarks | |
| Comp solution 1 | human albumin |
| identity | Cealb |
| supplier | CLB |
| formulation | solution for iv infusion, 20 g/100 ml |
| remarks | stored at 4oC, diluted with saline to 5 g/100 mL |
| Comp solution 2 | modified bovine gelatin |
| identity | Gelifundol |
| supplier | Biotest Pharma GmbH |
| formulation | solution, 5.5 g/100 ml |
| remarks | stored at 4oC, diluted with saline to 4 g/100 mL |

Laboratory Investigation
 a) Hematocrit was measured by centrifugation of blood in glass capillaries at 10.000 g for 5 min.
 b) Red Blood cell count was done with an electronic cell counter (model ZF; Coulter Electronics)

Calculations
 The hematocrit at each time point is calculated from the red blood cell count at that time point, the red blood cell (rbc) count at t=0 and the hematocrit at t=0.
 The expected (hypothetical) volumina are calculated as follows:
 i) expected blood volume (BV) is calculated assuming that no fluid shifts occur:
 at t=0 in ml: 65 (ml/kg)*body weight (kg)
 at t≧20: BV t=0–withdrawn volume+infused volume
 ii) expected plasma volume (PV) is calculated in ml assuming that no fluid shifts occur and that the body hematocrit is equal to that in the peripheral blood:
 at t=0 in ml : BV t=0*(1–hct t=0)
 at t≧20: PV t=0–withdrawn plasma+infused volume
 iii) expected hematocrit is calculated as (BV–PV)/BV
 The real volumes are estimated as follows:
 i) estimated real BV at t=0 as expected thereafter estimated from the ratio between the expected and the observed hematocrit:
 at t=0 in ml: 65 (ml/kg)*body weight (kg)
 at t>20: BV expect*exp hct/obs hct
 ii) estimated real PV at t=0 as expected thereafter estimated from calculated real BV and the observed hematocrit:
 at t+=0 in ml: BVt=0*(1–hct t=0)
 at t>0: estimated real BV*(1–hct)
 The volume expansion by the infused test solution at t=60 was estimated from the infused volume and the difference between the estimated real plasma volume and the expected plasma volume:
 i) volume expansion at t=60: infused volume–expected PVt=60+estimated real PVt=60
 ii) volume expansion per g colloid (ml/g)

Results and Discussion

Expansion of Plasma Volume

FIG. 1 shows the volume expansion after addition of a saline solution and after addition of a 5% human serum albumin (HSA) solution. The saline solution has a short lasting, limited effect and the HSA a significant long lasting oncotic effect, calculated from the hematocrit value which remained below the expected value throughout the observation period. For albumin, after 1 hour of infusion, an expansion of 30 ml/gram albumin was found in this model.

Figure 2:
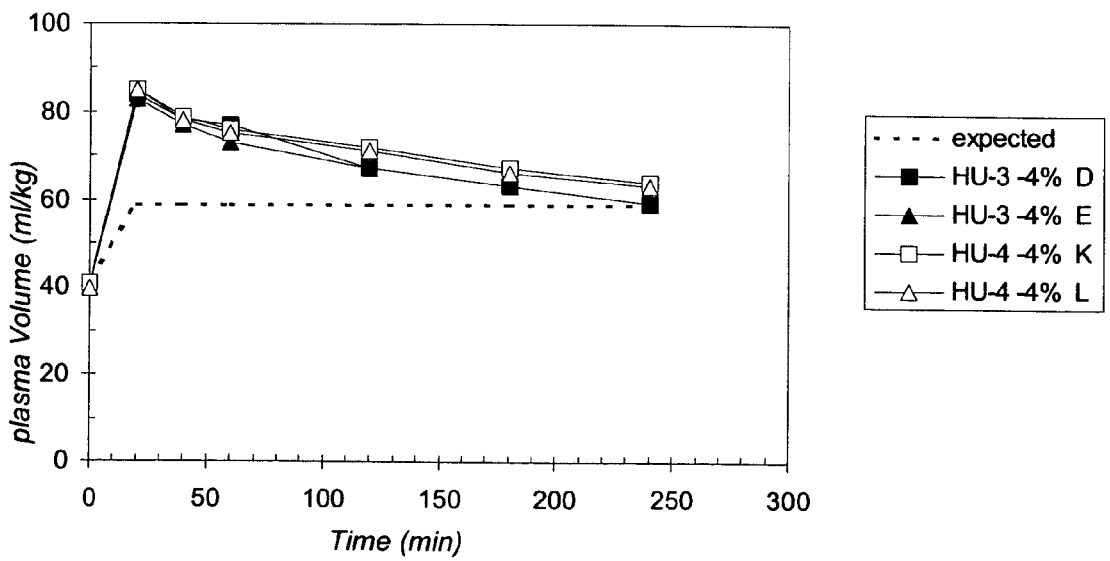
FIG. 2. Plasma volume expansion as a function of time after infusion of Hu-3 and Hu-4

FIG. 2 shows the volume expansion which is the effect of an infusion with a 4% solution of recombinant gelatin Hu-3 and Hu-4.

There is a clear hyperoncotic effect for both solutions, however, the hyperoncotic effect for Hu-3 has disappeared after 240 minutes, while the hyperoncotic effect for Hu-4 is longer lasting (up to 6 hours, not shown in this experiment). The only difference between Hu-3 and Hu-4 is their molecular weight, elucidating that the MW can be applied to steer the time span of the hyperoncotic effect. This remarkable effect is of high practical relevance for the clinical practice, for which a well controlled duration of the oncotic effect has been searched for in the past. Going from a MW of 55.2 kD to 73.6 results in an increase of the superoncotic effect from 4 hours to 6 hours.

Figure 3:
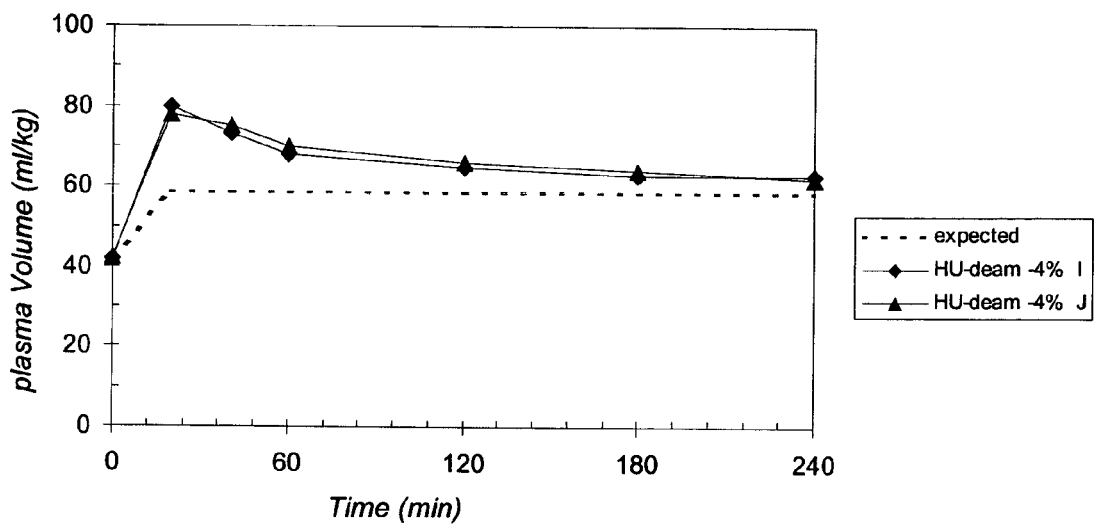
FIG. 3. Plasma volume expansion as a function of time after infusion with Hu-deam.

FIG. 3 shows the oncotic effect of Hu-deam measured in time. Hu-deam has a fully natural AA sequence in which the Gln and Asn amino acids are replaced by Glu and Asp amino acids by which the IEP is reduced from 9.7 to 4.6. This de-amidation is similar to the chemical de-amidation which is characteristic for the chemical modification of collagen into gelatin. The effect on the immunogenicity is limited or absent as was shown by the long clinical practice with gelifundol and other plasma expanders based on traditional gelatins.

This deamidation is a safe method to reduce the IEP of a natural collagen protein and increase the charge density. FIG. 3 shows that the hyperoncotic effect is lasting for more than 6 hours. This is longer than for Hu-3 (SEQ ID NO: 2). Hu-3 has a MW of 55.2 kD and Hu-deam (SEQ ID NO: 4) has a MW of 48 kD, by which example is shown that the charge density of the recombinant gelatin is an important factor by which the hyperoncotic effect can be manipulated. An increased charge density will result in an increased lapse time of the hyperoncotic effect. The Hu-deam has three additional point mutations in comparison with the natural sequence at position 108, position 318 and position 336 (Arg->Pro) to decrease the risk of proteolytic degradation, as it is known that each Arg residue represents a certain risk of a proteolytic cleavage (intra- or extracellularly) during the fermentation process.

Figure 4:
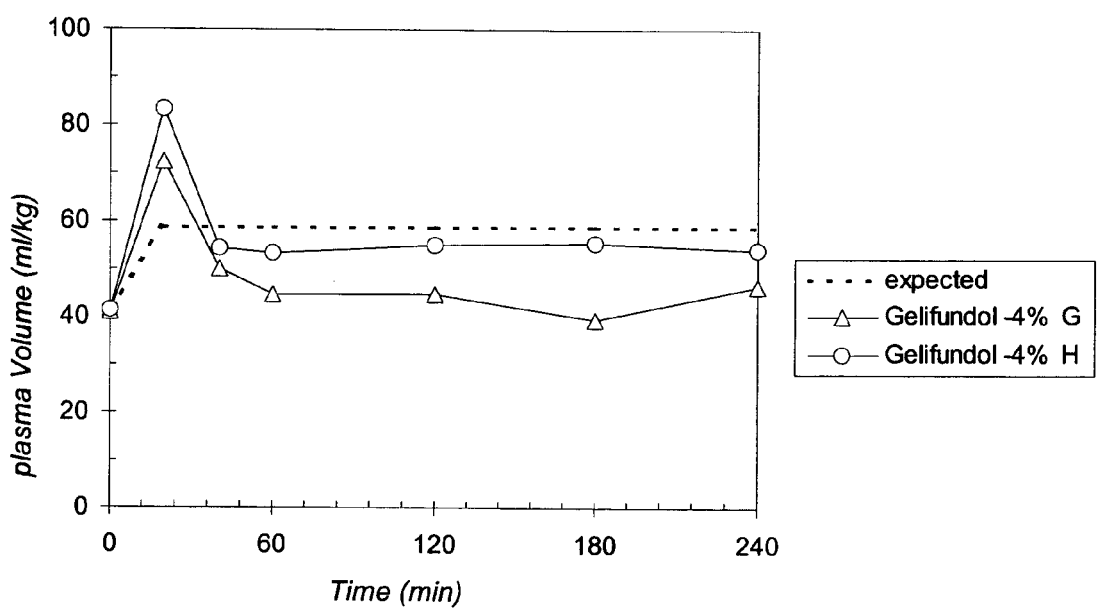
FIG. 4. Plasma volume expansion as a function of time after infusion with Gelifundol.

FIG. 4 shows the oncotic effect of Gelifindol added in a concentration of 4 g/100 ml. Gelifundol had a very short-lasting volume effect (FIG. 4). Also we found that the smaller fractions of the gelifundol appeared in the urine of the rats.

These results show clearly that the oncotic effect can be manipulated by the recombinant gelatin MW, and that multimerisation of the basic monomer is an effective method to increase the oncotic effect in practice. The oncotic effect of the Hu-2 (a dimer with a MW of 36.8 kD) was proven to be shorter than the oncotic effect of the trimer, but longer than of gelifundol (data not shown).

Moreover, a replacement of Gln and Asn by Glu and Asp appeared to be an effective method to increase the charge density by which it was found that the oncotic effect could be further increased.

Example 3

Radio Allergen Sorbent Test (RAS Test or RAST)

In order to demonstrate the presence of IgE antibodies against certain allergens or proteins the RAS test is used. For a detailed description of the RAS test reference is made to Aalberse et a J. Allergy Clin. Immunol., 1981, vol. 68: 356–364.

The compositions which contain gelatines that are tested are:

Gelofusine®, Gelifundol®, Composition containing Hu-3, Hu-4 and Hu-deam

Gelofusine® (modified gelatin 40g/l Na⁺ 154 mmol/l, Cl⁻ 125 mmol/l) and Gelifundol® (modified gelatin 55 g/l, Na⁺ 45 mmol/l, Cl⁻ 100 mmol/l, NaEDTA 0.19 g/l, Ca²⁺ 0.5 mmol/l, HCO₃⁻ 30 mmol/l) were used as commercially obtained.

Hu-3, Hu-4 and Hu-deam are described in example 1. Compositions comprising 55 g/l gelatin-like proteins Hu-3, Hu-4 and Hu-deam in PBS (Na⁺ 164 mmol/l. Cl⁻ 140 mmol/l, $HPO_4^-$ 10.9 mmol/l, $H_2PO_4^{2-}$ 1.8 mmol/l were prepared.

Sera of subjects which are known to have an allergy against specific foodstuffs were tested. The sera were selected on the known presence of IgE antibodies against foodstuffs, in particular against beef, pork and egg. Subjects having IgE antibodies against these foodstuffs possibly also have IgE antibodies against gelatin.

In addition 49 plasma samples obtained from plasmafereses, selected on the presence of IgE antibodies against known allergies, were tested.

The gelatin derivative or gelatin-like protein is conjugated to CNBr-activated Sepharose beads (Amersham Pharmacia Biotech, Uppsala, Sweden) (approximately 1 μg protein per mg beads) following a standard conjugation protocol according to the manufacturer's instructions.

Using a buffer containing Human Serum Albumin the concentration is adjusted to 2 mg beads per ml.

250 μl Sepharose beads conjugated to a gelatin derivative or a gelatin-like protein are incubated overnight at room temperature with 50 μl serum or plasma sample.

The beads are washed 4 times to remove excess serum or plasma and resuspended in 250 μl medium.

The beads are incubated overnight at room temperature with 50 μl anti-human IgE antibody labeled with $^{125}$I. The labeled IgE antibody is prepared following a standard procedure using chloramine T.

The beads are washed 4 times to remove excess $^{125}$I labeled anti-human IgE antibody. The reactivity in the samples is counted (with positive and negative controls). The presence of reactivity in a sample demonstrates binding of IgE in a serum or plasma to the gelatin derivative or gelatin-like protein and thus the risk of the occurrence of a hypersensitivity reaction.

| | Results | | | | |
|---|---|---|---|---|---|
| | Gelofusine ® | Gelifundol ® | Hu-3 | Hu-4 | Hu-deam |
| Serum 3093 | ++ | ++ | -- | -- | -- |
| Serum PF 175 | ++ | ++ | -- | -- | -- |
| Other sera | -- | -- | -- | -- | -- |

++ = specific immune reaction
-- = no immune reaction

In a control experiment the samples tested positive are pre-incubated with Gelofusine® or Gelifundol®. After pre-incubation, in the RAS test no radioactivity is found. The immunological reaction is specific for the gelatin derivatives used.

The invention claimed is:

1. A plasma substitute composition having a low blood clearance rate, the composition comprising a solution in saline, in a physiologically acceptable concentration, of a protein having a colloid osmotic function wherein the protein is a recombinant gelatin-like protein having a molecular weight of from at least 10,000 Daltons to at most 50,000 Daltons, having an isoelectric point of less than 8 and comprising at least one stretch of at least 10 consecutive Gly-Xaa-Yaa triplets, wherein at least 5% of the total number of protein amino acid residues are proline residues and wherein the protein is not crosslinked by chemical modification.

2. Composition according to claim 1 wherein the recombinant gelatin-like protein monomer has a molecular weight of from at least 15,000 Daltons to at most 25,000 Daltons.

3. Composition according to claim 1 wherein the recombinant gelatin-like protein has an isoelectric point of from at least 4 to at most 7.

4. Composition according to claim 1 wherein the recombinant gelatin-like protein has, at pH 8, a number of negatively charged amino acid residues and a number of positively charged amino acid residues such that the number of negatively charged amino acid residues, minus the number of positively charged amino acid residues is at least 2.

5. Composition according to claim 1 wherein said recombinant gelatin-like protein is a human gelatin-like protein.

6. Composition according to claim 1 wherein the recombinant gelatin-like protein with an isoelectric point of less than 8 is obtained by replacement of glutamine by glutamic acid and/or replacement of asparagine by aspartic acid in an amino acid sequence from a natural collagen protein.

7. Composition according to claim 1 wherein said recombinant gelatin-like protein comprises the amino acid sequence of SEQ ID NO: 1 or SEQ ID NO: 4.

8. Composition according to claim 1 wherein said recombinant gelatin-like protein comprises the amino acid sequence of SEQ ID NO: 2 or SEQ ID NO: 3.

9. The composition according to claim 1 wherein the recombinant gelatin-like protein has one or more features selected from the group consisting of: at least 5% of the total number of amino acids is a proline residue; 3-dimensional globular domains are absent; at least 10% of the total number of amino acids is a proline residue; at least 15% of the total number of amino acids is a proline residue; 5% of the total number of amino acids is a proline residue and the proline residues are evenly distributed; having sequences comprising proline residues which do not give rise to globular domains as determined by computer modeling; and a sequence comprising stretches of more than 20 amino acids without a proline residue.

10. A plasma-substitute composition having a low blood clearance rate, the composition comprising a solution in saline in a physiologically acceptable concentration, of a protein having a colloid osmotic function wherein the protein is a dimer or a timer or a tetramer of a recombinant gelatin-like protein monomer, the protein monomer having a molecular weight of from at least 10,000 Daltons to at most 50,000 Daltons, having an isoelectric point of less than 8 and comprising at least one stretch of at least 10 consecutive Gly-Xaa-Yaa triplets, wherein at least 5% of the total number of protein amino acid residues are proline residues and wherein said monomer, dimer, timer or tetramer is not crosslinked by chemical modification.

11. Composition according to claim 10 wherein said recombinant gelatin-like protein comprises the amino acid sequence of SEQ ID NO: 2 or SEQ ID NO: 3.

12. Composition according to claim 10 wherein the recombinant gelatin-like protein monomer has a molecular weight of from at least 15,000 Daltons to at most 25,000 Daltons.

13. Composition according to claim 10 wherein the recombinant gelatin-like protein has an isoelectric point of from at least 4 to at most 7.

14. Composition according to claim 10 wherein the number of negatively charged aminoacid residues at pH 8 in the recombinant gelatin-like protein, minus the number of positively charged amino acid residues at pH 8 in the recombinant gelatin-like protein is at least 2.

15. Composition according to claim 10 wherein said recombinant gelatin-like protein monomer is a human gelatin-like protein.

16. Composition according to claim 10 wherein the recombinant gelatin-like protein monomer with an isoelectric point of less than 8 is obtained by replacement of glutamine by glutamic acid and/or replacement of asparagine by aspartic acid in an amino acid sequence from a natural collagen protein.

17. Composition according to claim 10 wherein said recombinant gelatin-like protein comprises the amino acid sequence of SEQ ID NO: 1 or SEQ ID NO: 4.

18. A process for providing a plasma expander comprising dissolving in saline a recombinant gelatin-like protein with a molecular weight of from at least 10,000 Daltons to at most 50,000 Daltons, said recombinant gelatin-like protein having an isoelectric point of less than 8 and comprising at least one stretch of at least 10 consecutive Gly-Xaa-Yaa triplets, wherein at least 5% of the total number of protein amino acid residues are proline residues and wherein said protein is not crosslinked by chemical modification.

19. The process according to claim 18 wherein the recombinant gelatin-like protein has a molecular weight of from at least 15,000 Daltons to at most 25,000 Daltons.

20. The process according to claim 18 wherein the recombinant gelatin-like protein has an isoelectric point of from at least 4 to at most 7.

21. The process according to claim 18 wherein the number of negatively charged amino acid residues at pH 8 in the recombinant gelatin-like protein minus the number of positively charged amino acid residues at pH 8 in the recombinant gelatin-like protein is at least 2, optionally at least 3.

22. The process according to claim 18 wherein the recombinant gelatin-like protein is a human gelatin-like protein.

23. The process according to claim 18 wherein the recombinant gelatin-like protein comprises the amino acid sequence of SEQ ID NO: 1 or of SEQ ID NO: 2 or of SEQ ID NO: 3 or of SEQ ID NO: 4.

24. A process for providing a plasma expander composition having a low blood clearance rate, the process comprising dissolving a dimer or a trimer or a tetramer of a recombinant gelatin-like protein monomer in saline, the protein monomer having a molecular weight of from at least 10,000 Daltons to at most 50,000 Daltons, said recombinant gelatin-like protein having an isoelectric point of less than 8 and comprising at least one stretch of at least 10 consecutive Gly-Xaa-Yaa triplets, wherein at least 5% of the total number of protein amino acid residues are proline residues and wherein said protein is not crosslinked by chemical modification.

25. The process according to claim 24 wherein the recombinant gelatin-like protein monomer has a molecular weight of from at least 15,000 Daltons to at most 25,000 Daltons.

26. The process according to claim 24 wherein the recombinant gelatin-like protein has an isoelectric point of from at least 4 to at most 7.

27. The process according to claim 24 wherein the number of negatively charged amino acid residues at pH 8 in the recombinant gelatin-like protein minus the number of positively charged amino acid residues at pH 8 in the recombinant gelatin-like protein is at least 2, optionally at least 3.

28. The process according to claim 24 wherein the recombinant gelatin-like protein monomer is a human gelatin-like protein.

29. The process according to claim 24 wherein the recombinant gelatin-like protein comprises the amino acid sequence of SEQ ID NO: 1 or of SEQ ID NO: 2 or of SEQ ID NO: 3 or of SEQ ID NO: 4.

30. The process according to claim 24 comprising also employing recombinant gelatin-like protein monomer in a proportion to select a duration of the plasma expansion effect.

* * * * *